United States Patent [19]

Babson et al.

[11] Patent Number: 5,316,726
[45] Date of Patent: May 31, 1994

[54] AUTOMATED IMMUNOASSAY ANALYZER WITH PICTORIAL DISPLAY OF ASSAY INFORMATION

[75] Inventors: Arthur L. Babson, Chester; Arthur F. Ross, Mendham, both of N.J.; Douglas R. Olson, Doylestown, Pa.; Gershon Giter, Highland Park, Minn.; Victor R. Huebner, Newtown Square, Pa.

[73] Assignee: Cirrus Diagnostics, Inc., Chester, N.J.

[21] Appl. No.: 986,883

[22] Filed: Dec. 4, 1992

Related U.S. Application Data

[63] Continuation of Ser. No. 735,528, Jul. 26, 1991, abandoned.

[51] Int. Cl.$^5$ .................. G01N 21/13; G01N 21/76; G01N 21/01
[52] U.S. Cl. ........................... 422/65; 356/418; 364/188; 364/497; 364/500; 422/52; 422/63; 422/64; 422/67; 422/72; 436/45; 436/47; 436/172
[58] Field of Search .............. 198/502.3; 250/361 C; 356/414, 418, 224; 364/188, 478, 496, 497, 500, 516; 422/63–65, 52, 67, 72; 435/7.94; 436/45, 47, 164, 172

[56] References Cited

U.S. PATENT DOCUMENTS 2,421,344  5/1947  Mass ..................................... 356/414
3,285,703 11/1966  Narita et al. ......................... 422/52

(List continued on next page.)

FOREIGN PATENT DOCUMENTS 355738   2/1990  European Pat. Off. ........ 250/361 C
59-116046  7/1984  Japan ..................................... 436/47
61-291315 12/1986  Japan ................................. 198/502.3

OTHER PUBLICATIONS

R. M. Hecht et al. *J. Histochem. Cytochem.* 1981, 29, 771–774.

R. A. Bunce et al. *Analyst*, 1985, 110, 657–663.

E. H. Swift and E. A. Butler "Quantitative Measurements and Chemical Equilibria" 1972 W. H. Freeman and Company, San Francisco, Calif., 28–36.

A. Babson "The Cirrus Immulite ™ Automated Immunoassay System" *J. Clin. Immunoassay* 1991, 14, 83–88.

Primary Examiner—James C. Housel
Assistant Examiner—A. Soderquist
Attorney, Agent, or Firm—Whitham & Marhoefer

[57] ABSTRACT

An automated immunoassay analyzer includes a computer controlled instrument (10) and display (16). The display (16) provides a real-time presentation of all operations being performed within the instrument (10). A large number of samples can be loaded into the instrument (10), and the order of testing the samples can be rearranged according to a priority determined by the operator at any time. A wide variety of immunoassays can be performed on each sample and several different immunoassays can be performed on any one sample. Information related to the type of immunoassays being performed on particular samples is collected by a bar code reader (44) and this information is conveyed to the computer (12) for presentation on the display (16). The computer (12) tracks the progress of each immunoassay through the reaction circuit to the detection station (46). The time to completion for particular immunoassays as well as the concentration information for recently completed immunoassays is provided in a readily usable format. The immunoassay automation process is improved by performing the washing operation with an assay tube (26) which allows water to be expelled by centrifugal forces generated by rotating the tube about its longitudinal axis; rather, than by using more conventional aspirating equipment. Bound label is detected by chemiluminescence using a photomultiplier tube (96).

11 Claims, 6 Drawing Sheets

U.S. PATENT DOCUMENTS

| | | | |
|---|---|---|---|
| 3,587,676 | 6/1971 | Oehlin et al. | 422/65 X |
| 3,722,790 | 3/1973 | Natelson | 422/101 X |
| 3,838,809 | 10/1974 | Williams | 422/101 X |
| 3,854,879 | 12/1974 | Figueroa et al. | 436/47 |
| 4,007,011 | 2/1977 | Greaves et al. | 422/64 X |
| 4,039,286 | 8/1977 | Keller et al. | 422/67 X |
| 4,066,412 | 1/1978 | Johnson et al. | 422/65 |
| 4,166,095 | 8/1979 | Kling et al. | 422/67 |
| 4,265,855 | 5/1981 | Mandle et al. | 422/65 |
| 4,451,433 | 5/1984 | Yamashita et al. | 422/67 X |
| 4,459,265 | 7/1984 | Berglund | 436/47 X |
| 4,558,953 | 12/1985 | Yamada | 356/414 X |
| 4,628,470 | 12/1986 | Baumann | 364/188 X |
| 4,647,432 | 3/1987 | Wakatake | 422/67 X |
| 4,731,225 | 3/1988 | Wakatake | 422/67 X |
| 4,754,414 | 6/1988 | Gokho | 422/62 X |
| 4,764,342 | 8/1988 | Kelln et al. | 436/45 X |
| 4,818,883 | 4/1989 | Anderson et al. | 436/172 X |
| 4,863,690 | 9/1989 | Berthold et al. | 422/52 |
| 4,871,683 | 10/1989 | Harris et al. | 435/7.94 X |
| 4,978,614 | 12/1990 | Bronstein | 435/810 X |
| 5,084,240 | 1/1992 | Babson | 422/72 |

AUTOMATED IMMUNOASSAY ANALYZER WITH PICTORIAL DISPLAY OF ASSAY INFORMATION

CROSS-REFERENCE TO RELATED APPLICATIONS

This application is a continuation of U.S. patent application Ser. No. 07/735,528 filed Jul. 26, 1991, now abandoned.

This patent application is related to the U.S. patent application Ser. No. 552,063 filed Jul. 13, 1990, now U.S. Pat. No. 5,084,240, and the U.S. patent application having Ser. No. 552,132 filed Jul. 13, 1990, now U.S. Pat. No. 4,098,845, and both of those applications are herein incorporated by reference.

BACKGROUND OF THE INVENTION

1. Field of the Invention

The present invention generally relates to automated immunoassay analyzers and, more particularly, to an automated immunoassay analyzer which provides a scientist or technician with an easily understandable presentation of all of the operations occurring within the analyzer at any time.

2. Description of the Prior Art

An immunoassay is a well known laboratory method used to determine the amount of an analyte in a sample such as plasma or urine. It is based on the interaction of antibodies with antigens, and because of the degree of selectivity for the analyte (either antigen or antibody), an immunoassay can be used to quantitatively determine very low concentrations of drugs, hormones, polypeptides, or other compounds found in a test sample. For many years, immunoassays were performed by hand by trained laboratory technicians.

Recently, many companies have begun producing automated immunoassay analyzers. Automating the immunoassay procedures has been difficult because of the large number of steps which need to be performed. For example, a sample is mixed with a reagent and a solid support having a bound antigen or antibody, the sample is incubated such that the corresponding antigen or antibody in the sample and a labelled antigen or antibody provided in the reagent can be bound to the antigen or antibody on the solid support, then the solid support is thoroughly washed and the label (fluorescent, radioactive, chemiluminescent, or the like) is detected by an appropriate mechanism, and finally the analyte of interest (antigen or antibody) is quantified from the detected label.

One of the chief stumbling blocks for performing the automated immunoassay has been the step of thoroughly washing the solid support. In immunoassays, it is essential that the free label and bound label be completely separated prior to detection of the bound label or erroneous results will occur. Many of today's automated immunoassay analyzers utilize high speed pipetting and aspirating stations for the washing operation. Pipetting and aspirating wash fluid into and out of a sample container requires a large number of mechanized parts. Moreover, it is very difficult to completely remove all sample and wash fluid from a reaction chamber via aspiration; therefore, an automated system which uses such a wash station may be subject to some detection errors.

Most of today's automated immunoassay analyzers are designed for "walk away" operation. That is, a technician loads sample containing tubes onto a carousel and presses a start button. Thereafter, the automated immunoassay analyzer mixes appropriate reagents (which are often stored on-board the analyzer) with the sample, performs incubating and washing operations, detects the label, and computes the quantity of analyte in the sample from the detected label and stored calibration curves. The entire operation is typically done under computer control, and in some automated immunoassay analyzers, bar coding is used to identify the sample under test. The results of the immunoassays are typically output onto computer paper for inspection by the technician. Hence, the technician is free to perform other functions around the laboratory while the analyzer is functioning. In addition, the immunoassays may be performed overnight without the supervision of the technician.

Since most automated immunoassay analyzers have been designed with the thought in mind that the immunoassay will be performed unattended and the results examined later, they do not optimally serve the operational needs of most scientists and technicians. That is, most scientists and technicians would like to check the operation of an instrument periodically and have an understanding of the functions being performed. Having knowledge of some test data while the analyzer is still performing other operations on the remaining test samples, as well as an understanding of when a particular task will be finished by the analyzer, often helps scientists or technicians plan their investigations for that day. If interesting results are noted early in the morning, then the scientist or technician can channel his or her efforts immediately, rather than being required to wait until the entire batch of assays is completed. Moreover, If the scientist or technician needs to know results quickly, it would be ideal for him or her to be able to determine when an immunoassay will be completed by the analyzer and be able to prioritize certain immunoassays over others remaining to be performed.

SUMMARY OF THE INVENTION

It is therefore an object of the invention to provide an improved automated immunoassay analyzer.

It is another object of the invention to provide an automated immunoassay analyzer which is not hampered by an aspirating operation for washing the biomaterial with bound analyte.

It is still another object of the invention to provide an automated immunoassay analyzer with a means for presenting in real-time all the operations occurring within the analyzer such that an operator has an understanding of which tests are being performed, how long they will take to complete, and the results of some of the immunoassays which have been completed by the analyzer.

According to the invention, an improved automated immunoassay analyzer is provided. In the automated immunoassay analyzer, a unique assay tube is utilized for performing the immunoassays which allows sample and wash fluid to be expelled without aspiration. Use of the assay tube speeds up the washing operation and allows for more reliable results. The automated immunoassay analyzer has a computer control which controls the selection of reagents for performing a variety of immunoassays on a number of different samples which are loaded into the analyzer. In addition, the computer controls the timing of incubation, mixing, washing and detection operations, as well as tracks the progress of each immunoassay being performed in the analyzer at any one time. A display connected to the computer provides an operator with information concerning all the operations being performed by the analyzer in an easy to understand format in real time.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF A PREFERRED EMBODIMENT OF THE INVENTION

Figure 1:
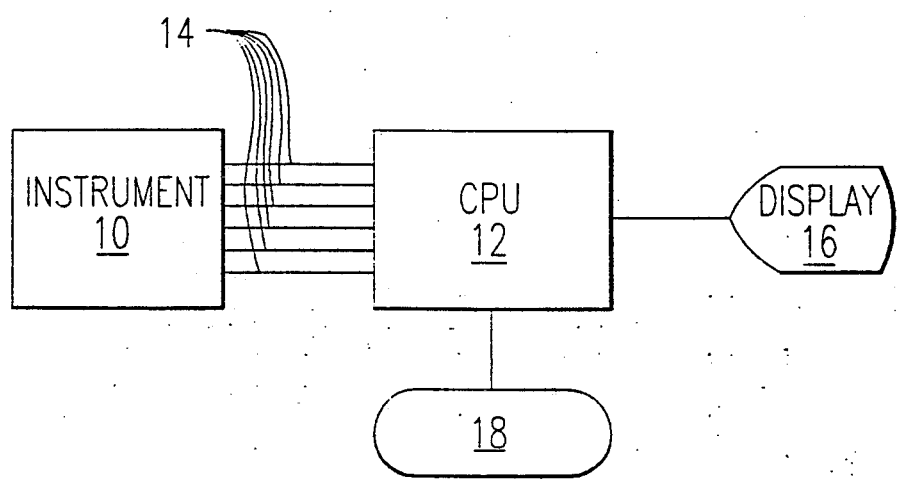
FIG. 1 is generalized block diagram of the automated immunoassay analyzer.

Referring now to the drawings, and more particularly to FIG. 1, there is shown a generalized block diagram of the automated immunoassay analyzer wherein the instrument 10 which actually performs the immunoassays on multiple samples is connected to a computer 12 via data communication lines 14. The data communication lines 14 are used to supply information from the instrument 10 to the computer 12 such as bar coded information on the reagent and assay tubes as well as photon counts measured by a photomultiplier tube. The instrument 10 is preferably operated under the direction of on-board microprocessors (not shown). The operations of the instrument 10 and computer 12 will be discussed in more detail in conjunction with FIGS. 2 and 3. The computer 12 is connected to a display 16 which presents the operator with a real time synopsis of all operations occurring within the instrument 10. The display 16 will be discussed in more detail in conjunction with FIG. 7. A keyboard 18 may be provided for the operator to input patient information associated with test samples or to perform other analysis and control functions.

Figures 4, 5, 6:
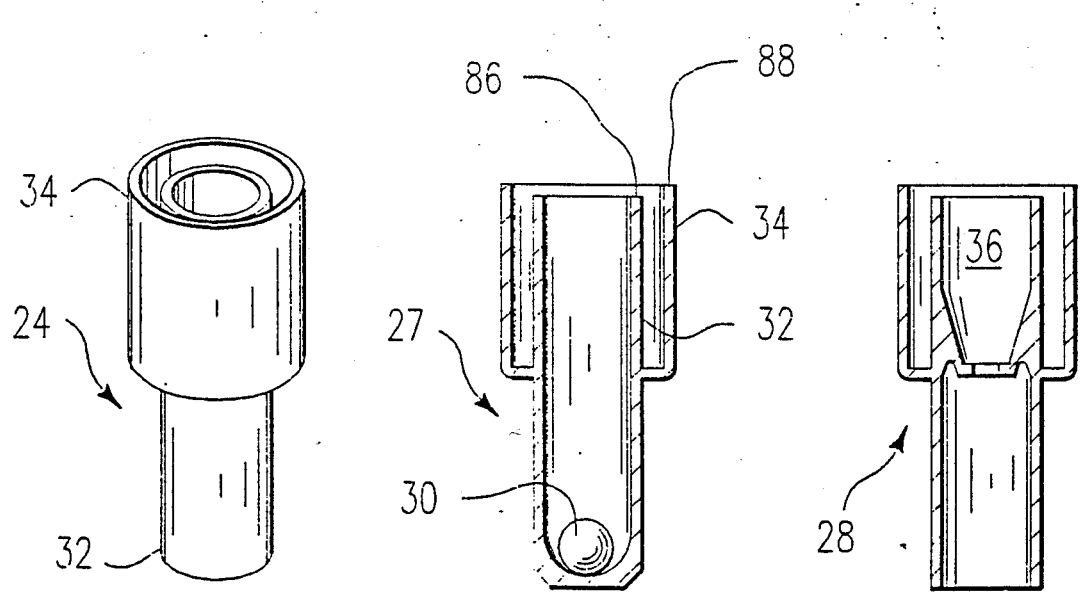
FIG. 4 is an isometric view of an assay tube.
FIG. 5 is a cross-sectional side view of an assay tube.
FIG. 6 is a cross-sectional side view of a sample cup carrier.
Figure 2:
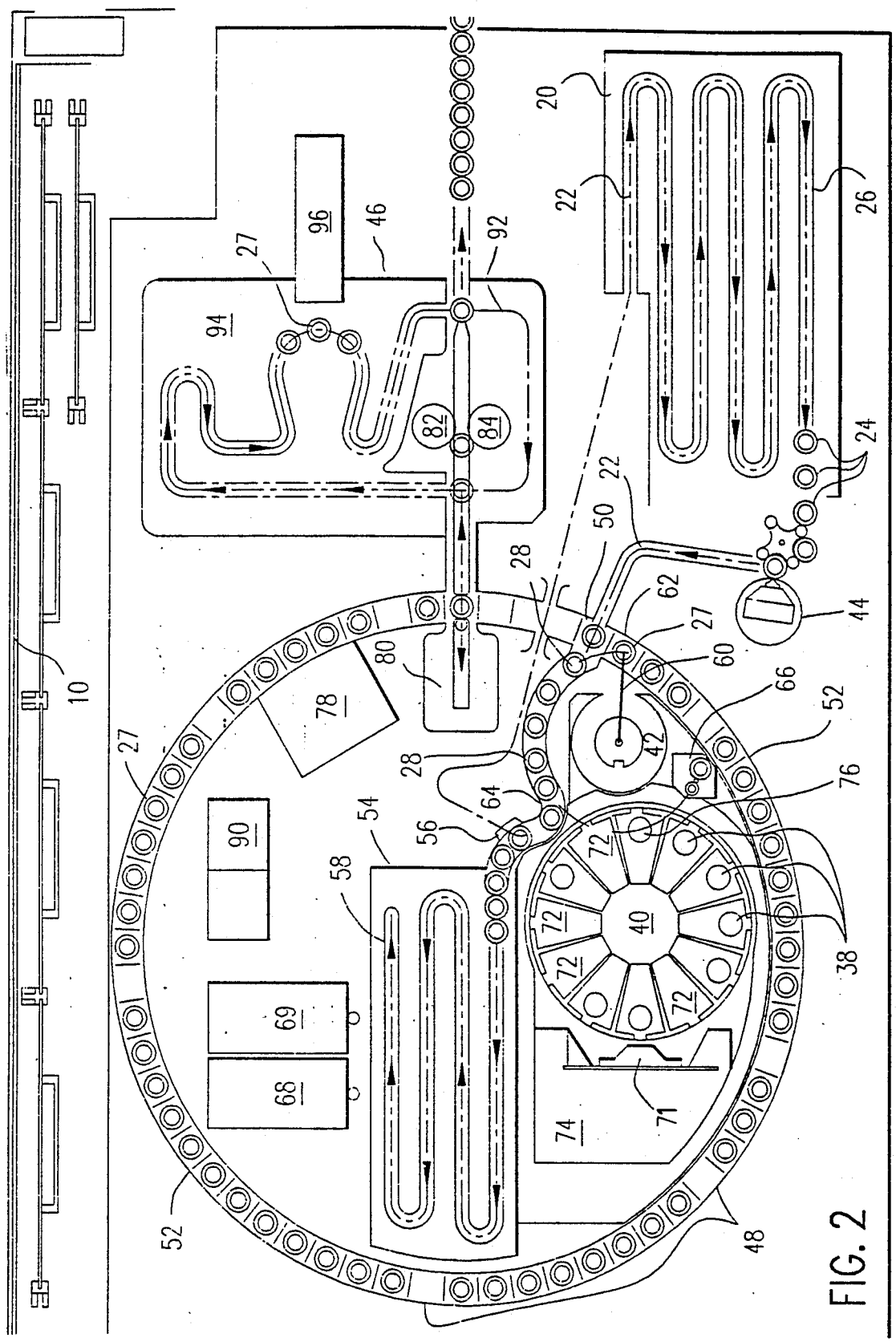
FIG. 2 is a block diagram of the flow path of samples and assays through the automated immunoassay analyzer.

FIG. 2 shows the internal details of the instrument 10. A loading platform 20 includes a continuous loading chain 22 in which sample and assay tubes 24 are placed. The loading chain 22 is preferably laid out in a serpentine channel 26 to accommodate a large number of tubes 24 for testing. The tubes 24 are shown in detail in FIG. 4. These tubes 24 include a central tube 32 having a first diameter and a waste chamber 34 having a larger, second diameter than the central tube 32. The tubes 24 may either be used for performing immunoassays or for carrying samples. FIG. 5 shows the cross-section of an immunoassay tube 27 and FIG. 6 shows the cross-section of a sample carrier tube 28. Because the immunoassay tube 27 and sample carrier tube 28 have the same external dimensions, they are carried on the loading chain 22 (FIG. 2) in the same manner. The assay tubes 27 of FIG. 5 are described in detail in the co-pending U.S. patent applications having Ser. Nos. 552,063 and 552,132 filed Jul. 13, 1990, and include a biomaterial bound to an inert support 30 (e.g., a polymeric bead) in the bottom of a central tube 32 which has an attached waste fluid collection chamber 34. The biomaterial is an antigen or antibody which will be selective for a particular analyte whose quantity is to be determined by immunoassay. The sample carrier tubes 28 of FIG. 6 have a central cavity 36 for receiving sample cups, such as product No. 127-0093010 sold by Evergreen Scientific, Los Angeles, Calif.

With reference to FIG. 2 and FIGS. 4 through 6, the tubes 24 are arranged in the loading chain 22 with a sample carrier tube 28 followed by several assay tubes 27. In this manner, several different immunoassays can be performed on the same sample by pipetting sample from the lead sample carrier tube 28 into each of the following assay tubes 27, where each assay tube 27 may be selected to test for a different constituent in the sample. It is anticipated that many different constituents in the sample can be tested by immunoassay depending on the selection of the biomaterial bound to the inert support 30 in the assay tube 27. For example, digoxin (DIG), thyrotropin (TSH), human chorionic gonadotropin (hCG), thyroxine (T4), and many other constituents can be assayed by appropriate selection of the biomaterial in the assay tube 27 and the reagents 38 in the reagent carousel 40 of the instrument 10. As the tubes 24 are transported by the loading chain 22 towards the pipetting station 42, they pass through a bar code reader 44. The bar code reader 44 identifies the sample number from sample carrier tube 28 and the immunoassay test to be performed in each assay tube 27 as well as the lot number of the assay tube 27.

With reference to both FIGS. 1 and 2, information from the bar code reader 44 is sent to the computer 12 which tracks the position of the tube 24 within the instrument 10 and the contents of the tube 24. Position information can be derived from the total number of spaces in the path to be travelled by the tubes 24 from the bar code reader 44 to the detection station 46. Not all the spaces in the loading chain 22 need to be filled with a tube 27 since the bar code reader 44 will simply identify an empty space in the path to the computer 12, and the computer can simply track an empty space 48 during normal incremental advancements of the tubes 27 towards the detection station 46. In addition, an empty sample tube (not shown) can be provided behind the sample carrier tube 28 to allow a dilution of the sample to be performed in the sample tube. In such case, the identity of the empty sample tube would be indicated to the computer 12 by the bar code reader 44, and the computer 12 would track the empty sample tube to the pipetting station 42, whereupon instructions for the dilution would be fed from the computer 12 to the pipetting station 42.

The automated immunoassay analyzer allows the operator to easily rearrange the tubes 24 on the loading platform 20 if there is a need to obtain quicker results for one sample as opposed to another. This is accomplished simply by moving the sample carrier 28 for the sample of pressing interest and its trailing assay tubes 27 to the front of the serpentine channel 26 while moving other groups towards the rear. By providing easy access to the tubes 24 in the loading chain 22, the operator can make the appropriate changes in assay priority while the analyzer is in operation.

At juncture 50, a transfer of the tubes 24 from the loading chain 22 to the incubation carousel 52 may occur. The computer 12 is informed of the contents of a tube 24 at the bar code reader 44 and is programmed to recognize the number of incremental advancement positions there are along the loading chain 22 between the bar code reader 44 to juncture 50. Upon arrival at juncture 50, if the tube 24 is a sample carrier tube 28 (as shown in FIG. 6), the computer 12 directs the instrument 10 to allow the sample carrier tube 28 to continue on the loading chain 22 towards the sample collection station 54. Towards the front of the collection station 54, a deflector 56 directs the tubes 28 of used sample off the loading chain 22 and into a serpentine channel 58 of the collection station 54. The tubes 28 in the collection station 54 can be removed and disposed of at the convenience of the operator either after the analyzer has run all samples (i.e., in the morning after an overnight run) or while the analyzer is running (which can occur if the operator notices the collection station 54 is becoming full of waste tubes). Conversely, if the tube 24 at juncture 50 is an assay tube 27 (as shown in FIG. 5), it is transferred to the incubation carousel 52 and continues on to perform a prescribed immunoassay on the sample.

With particular reference to the pipetter station 42 in FIG. 2, it can be seen that a pipetting arm 60 travels a circular path from which it can access an assay tube 27 in the incubation carousel 52 at location 62, a sample carrier tube 28 located at any of five positions in the arcuate channel 64, a reagent 38 in the reagent carousel 40, and a probe wash station 66. A downward projecting pipette tip (not shown) is positioned at the free end of the pipetting arm 60. To perform pipetting operations, the pipette tip must be inserted into and out of the tubes 24 and reagents 38 by translating the arm 60 along its Z-axis (perpendicular to the plane of the paper). The amount of Z-axis translation of the pipetting arm 60 is closely controlled by a level sensing scheme (not shown) so that the pipetter can be assured of dipping into the sample container 28 or reagent bottle 38 far enough to siphon up the correct amount of sample or reagent, but shallow enough not to damage the operations of the pipetting station 42 or corrupt the pipetter with sample or reagent which may be carried over to the next assay tube 26. In a preferred embodiment, the sample carrier tube 28 can be made of a carbon filled polypropylene such that they will have electrical properties that allows capacitance level sensing to be performed.

Two precision syringe pumps 68 and 70 are connected to the pipetting station 42. Preferably, one of the syringe pumps 68 or 70 is calibrated for large volumes while the other is calibrated for small volumes. The probe wash station 66 has separate wash wells for simultaneously flushing the inside and outside of the pipette tip. Extensive probe flushing on every pipetting cycle eliminates detectable sample carryover. The probe wash station 66 also has a fresh water supply. In a preferred embodiment, the pipetter may pick up one or more small air bubbles separated by water to aid in the transfer of sample and reagent to the assay tube 26.

The operation at the pipetting station 42 requires selecting an appropriate reagent 38 from the reagent carousel 40. The contents of the reagent carousel 40 are tracked by the computer 12 (FIG. 1) via input from the bar code reader 71 which senses lot specific information from the bar codes on each of the reagent bottles 38. The carousel 40 holds up to twelve reagent bottles 38, each of which preferably has sufficient reagent for performing 50–100 tests. The reagents 38 may be cooled thermoelectrically, if required, by the thermoelectric cooler 74. The carousel 40 need not be completely loaded with reagents 38 since the location of an empty position 72 on the carousel 40 will be tracked by the computer 12 in the same manner as location of each of the reagents 38 on the carousel 40. Periodically, the entire contents of the carousel 40 is scanned by the bar code reader 71 and position-specific information is sent to the computer 12.

When a sample carrier tube 28 reaches the arcuate channel 64 and an assay tube 27 is in position in the incubation carousel 52, the pipetting arm 60 is rotated to the reagent carousel 40, and the reagent carousel 40 is indexed such that the appropriate reagent 38 will be at position 76. Thereupon, the pipetting arm 60 is lowered into the reagent bottle 38, and an appropriate amount of reagent is siphoned into the pipetting tip. Thereafter, the pipetting arm 60 is raised out of the reagent bottle 38, rotated to the pipette wash station 66, lowered into the wash well, and the outside of the pipette tip is washed to remove any excess reagent. Then the pipetting arm is raised out of the wash well, rotated to the sample carrier tube 28, the pipette tip is dipped into the sample, and the appropriate amount of sample is retrieved.

Preferably, sample, reagent and water in a total volume of 250 µl are transferred simultaneously to the assay tube 27 at location 62 of the incubation carousel 52. This insures that the competing reactions between the antigens or antibodies of interest in the sample and the assay specific antigens or antibodies of the reagent 38 with the bound biomaterial in the assay tube 26 start simultaneously. In a preferred embodiment, the reagent 38 is highly concentrated so that a greater amount of distilled water from the syringe pumps 68 and 70 can be added to the assay tube 27 along with the sample and reagent. Adding large quantities of distilled water promotes rinsing the pipettor 60 tip. The proportions of the sample, reagent and water depend on the immunoassay to be performed and is a function of the antibody bound on the inert support. Table 1 provides exemplary amounts of sample, reagent, and water for a small number of the many different immunoassays which can be performed with the present automated immunoassay analyzer.

TABLE 1

| Analyte | Reagent | Sample | Water | Total |
|---------|---------|--------|-------|-------|
| Digoxin | 100 µl | 50 µl | 100 µl | 250 µl |
| hCG | 50 µl | 10 µl | 190 µl | 250 µl |
| T4 | 50 µl | 10 µl | 190 µl | 250 µl |

Obviously, alternative proportions of the components to be pipetted into the assay tube 27 can be used.

If several different immunoassays are to be performed on one sample, the pipetting arm 60 will access the sample carrier tube 28 as it progresses through the arcuate channel 64 during the simultaneous incremental advances of the loading chain 22 and incubation carousel 52. While the sample carrier tube 28 is shown to be accessible by the pipetting station 42 in any of five different positions in the arcuate channel 64 of FIG. 2, the total number of positions in the arcuate channel 64 can vary with the design of the analyzer to accommodate more than five different immunoassays being performed on any one sample.

The incubation carousel 52 is incremented every thirty seconds and has a throughput of 120 assay tubes per hour. The incubation carousel 52 is heated to 37° C. and periodically shaken such that the antigen-antibody specific reactions occurring in the assay tubes 27 are promoted. In the preferred embodiment, the assay tubes 27 are shaken every ten seconds to maximize the rate of the immunological reactions. Carousel drive 78 is operated according to computer instructions and performs the incremental advancement and agitation functions. The time for an assay tube 27 to traverse the incubation carousel 52 is dependent on its size and number of incremental advancement positions. In a preferred embodiment, it takes thirty minutes for an assay tube 27 to make a complete circuit of the carousel 52, which is the incubation time for most analytes. Computer algorithms can be provided which would allow assay tubes 27 which are performing tests such as TSH which require very high sensitivity to make a second circuit of the carousel 52 for a one hour incubation time.

After incubation, the assay tubes 27 are shuttled out of the incubation carousel 52 by a lateral transfer shuttle 80 or by other suitable means and installed in a high speed spin station noted on FIG. 2 as a high speed driver 82 and an idler 84. Washing the bound biomaterial on the inert support 30 at the base of the assay tube 27 is performed at the high speed spin station. With reference to FIG. 5, the assay tube 27 is spun about its longitudinal axis at high speed, whereby the sample fluid climbs up the outwardly tapered inside wall of the central tube 32 under centrifugal forces and is sprayed outwardly over the top end 86 and is collected in the waste chamber 34. A cover (not shown), which may either be penetrable by the pipette tip of pipette station 42 or be provided with an opening of smaller diameter than the top end 86 of the central tube 32, is affixed to the top end 88 of the waste chamber 34 and extends over the central tube 32 so the sample fluid does not spray out of the assay tube 27 during high speed rotation. The cover should be positioned close enough to the top end 86 of the central tube 32 that if the inert support 30 in the base of the central tube 32 is a bead which is unattached to the central tube 32, the inert support 30 with the bound biomaterial will not be washed over into the waste chamber 34 during longitudinal rotation of the assay tube 27. Wash water is added to the central tube 32 via a solenoid wash pump 90 pipetting volumes of water straight down into the central tube 32. High speed rotation of the assay tube 27 is again used to remove the wash water from the central tube 32. In a preferred operation, multiple 200 82 l volumes of water (e.g; four volumes) are pipetted into the central tube. After each addition, the wash water is almost instantaneously removed after washing the inert support 30 with the bound biomaterial by high speed rotation of the tube 27. The use of assay tube 27 shown in FIG. 5 greatly facilitates the washing operation required in performing an immunoassay and represents a significant improvement over the use of aspiration equipment in an automated immunoassay analyzer environment. In particular, removal of the sample and wash fluid in the above-described manner allows the wash operation to be performed more quickly and with better precision (i.e., it will be easier to remove all the fluid by high speed rotation than by aspiration). After washing, the assay tube 27 and inert support 30 will be free of unbound labelled reagent so that only bound labelled reagent will be detected.

Washed assay tubes 27 are transferred to the detection station 46 for quantification of the analyte of interest. In the preferred embodiment, chemiluminescent techniques are used to quantify the analyte. Therefore, it is preferable to label the assay specific antigen or antibody in the reagent 38 with alkaline phosphatase which will be used to cleave a phosphate ester stabilized dioxetane. Decomposition of the dioxetane results in the emission of light photons which can be quantified at the detection station 46 and are proportional to the quantity of analyte present. However, it should be understood that other detection schemes such as fluorescence or radioactive ion emission could be used and appropriate labeling of the reagent 38 is required. In the detection station 46, the assay tubes 27 are advanced by a continuous chain 92 similar to that used in the loading station 20. The chain 92 traverses a tortuous path that excludes ambient light and provides a ten minute incubation to develop the luminescent signal. Preferably, the luminometer block 94 is heated to 37° C. Once the assay tube 27 has advanced to a position in front of the photomultiplier tube 96, the photon counts are measured.

One advantage of the chemiluminescent alkaline phosphatase reaction described above is that it provides for extreme sensitivity of the assay. However, the nature of immunoassay is that the concentration of analytes of interest varies over a wide dynamic range. The inventors have recognized that the extreme sensitivity of the assay may not always be desirable for quickly determining the concentration of the analyte and have contemplated an automated procedure for adjusting the dynamic range of the photomultiplier tube 96.

Figure 10:
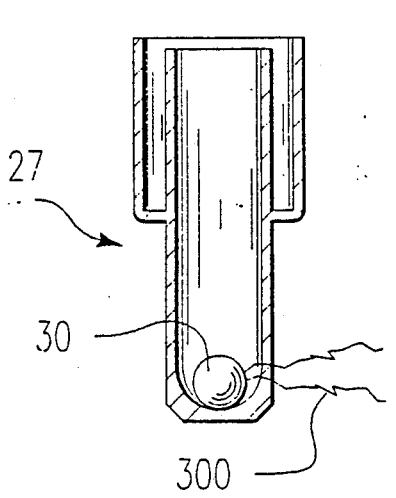
FIG. 10 is a block diagram of a photomultiplier tube measuring chemiluminescent light intensity from bound label in an assay tube where automatic attenuation is provided.
Figure 10:
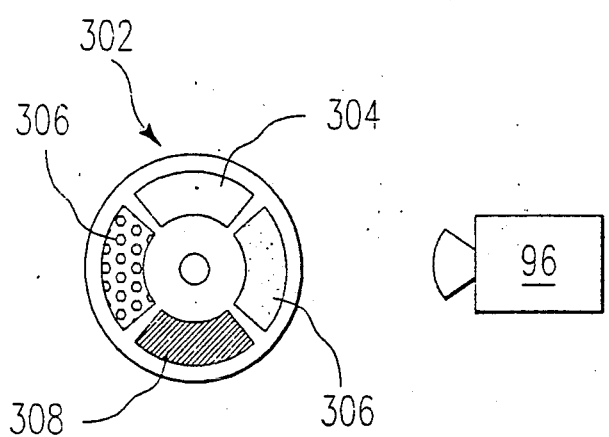

FIG. 10 shows an embodiment of the invention where automated attenuation of the light signal 300 from the bound labeled analyte on the inert support 30 in the assay tube 27 is achieved using a filter wheel 302. The filter wheel preferably has an open section 304 for making unattenuated counts, one or more neutral density filters 306 for making attenuated counts, and an opaque region 308 for making dark count measurements. Dark counts are used to calibrate for "noise" in the photomultiplier tube 96 (e.g., counts made with opaque region 308 in place are "noise"). Preferably, one of the filters 306 is a 2A filter (a one hundred fold attenuator). In a particular embodiment, a one hundred-fold attenuator 306 is positioned in front of the photomultiplier tube 96 to reduce the detected light. If the number of counts obtained are below a set level, the attenuator is automatically removed (by the wheel 302 rotating the opening 304 into alignment) and the photons emanating from the assay tube 27 are recounted without attenuation. In this way, the dynamic range is increased by two orders of magnitude. If other filters 306 are provided, where the other filters 306 can be 1A, 3A, 4A, etc., the dynamic range of the photomultiplier tube can be greatly increased. Preferably, the counts are measure for twelve consecutive one second intervals, and the highest and lowest counts, which can be considered outlier measurements, are discarded and the remaining ten measurements are averaged.

The average counts per second are converted to analyte concentration by the computer 12 using stored standard curves which mathematically relate photon counts to concentration. The photon count and concentration information for each assay tube 27 is archived to a magnetic storage device for later analysis. The concentration for the assay tube 27 is also sent to display 16 by computer 12. Periodic calibration with known calibrating solutions maintains the mathematical relationship for a particular instrument 10 and lot of reagents 38. Calibration of the standard curves may performed by placing a fluid with a high concentration of a compound to be assayed (e.g., DIG, TSH, etc.) in a sample carrier tube 28 followed by three assay tubes 27 and placing a fluid with a low concentration of the compound to be assayed in another sample carrier tube 28 followed by another three assay tubes 27. The tubes will then be processed in the same manner described above for test samples wherein a volume of the high concentration compound will be reacted in each of its three trailing assay tubes 27 and a volume of the low concentration compound will be reacted in each of its three trailing assay tubes 27. After the photon counts for each of the high concentration compound assay tubes 27 are determined, they are averaged to provide a high point on the standard curve. Likewise, after the photon counts for each of the low concentration compound assay tubes 27 are determined, they are averaged to provide a low point on the standard curve. It is anticipated that all normal test samples will have photon counts which lie between the high and low points on the standard curve. In order to update the standard curve in the computer 12 via the calibration run, the technician must input the calibration run information into the computer 12 prior to performing the calibration run.

Figure 3:
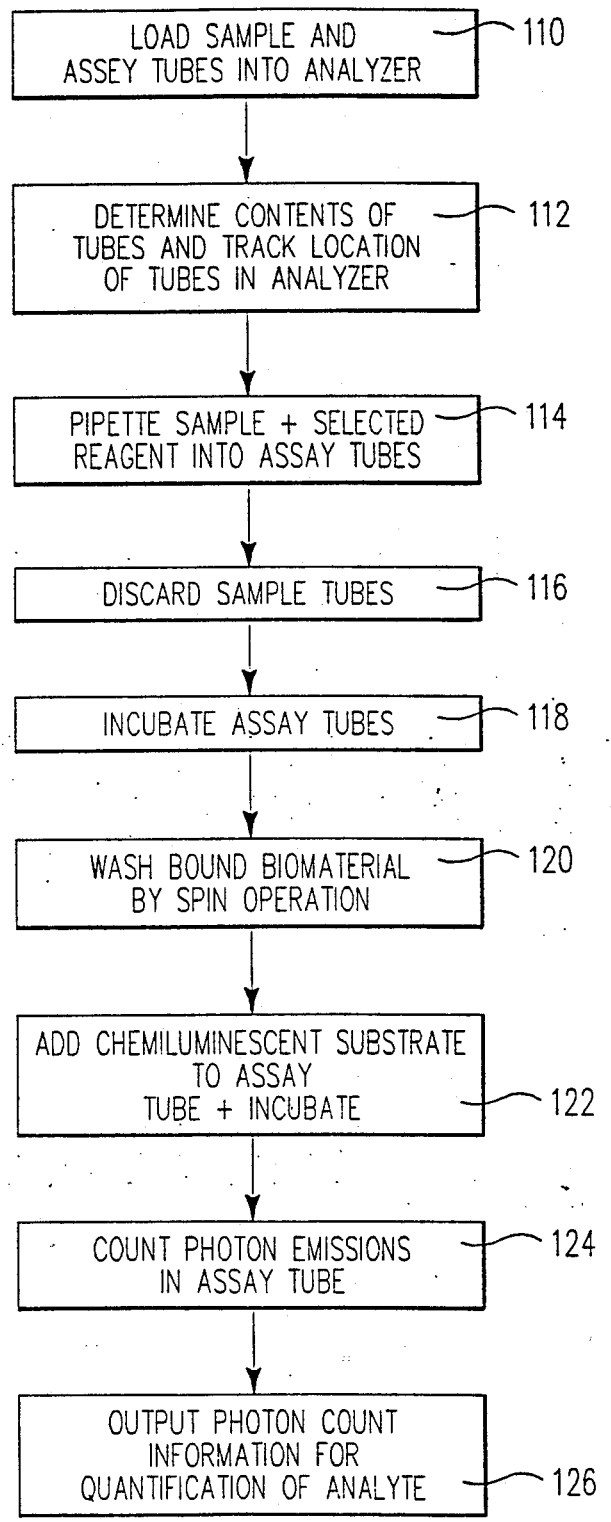
FIG. 3 is a flow chart of the processing steps performed on the assay tubes in the automated immunoassay analyzer.

FIG. 3 illustrates the process steps performed by the instrument 10 of the automated immunoassay analyzer. First, at step 110, the tubes are loaded onto the loading chain at the loading station. Because of the easy access to the loading station, the scientist or technician can prioritize assays to be performed by placing a sample and assay tubes of interest at the front of the loading chain. Second, at step 112, the contents of each of the tubes is determined by a bar code reader. Once the identity of the tube is determined (sample or assay tube), the location in the immunoassay analyzer is tracked. Since the circuit has a predetermined number of incremental positions from the bar code reader to the detector, the precise location of a particular assay tube and the immunoassay being performed is known at all times. At step 114, when a sample tube and its associated assay tube are in the proper position, the sample and the appropriate reagent are obtained by the pipetter and deposited in the assay tube. At step 116, sample tubes which have been used are discarded. At step 118, assay tubes which have been combined with sample and reagent are incubated. The time of incubation is determined by the dimensions of the incubation carousel and time for incremental advancements in the analyzer. At step 120, assay tubes which have been incubated for the requisite period of time are transferred to a high speed washing station. Washing is achieved by rotating the assay tubes about their longitudinal axes and by pipetting wash water into the assay tubes. High speed rotation of the tubes causes wash fluid to be rapidly removed from the inert support carrying the bound biomaterial which has the bound reagent label. After washing, a chemiluminescent substrate (phosphate ester dioxetane) is added to the assay tube at step 122, and the assay tube is incubated again for a short time. During incubation, alkaline phosphatase from the reagent which is bound to inert support 30 cleaves the phosphate ester of the chemiluminescent substrate. Decomposition of the dioxetane releases photon energy. After decomposition of the dioxetane, the photon emissions are counted at step 124 by a photomultiplier tube. At step 126, photon count information is sent to the computer for quantitative determination of the analyte.

Figure 7:
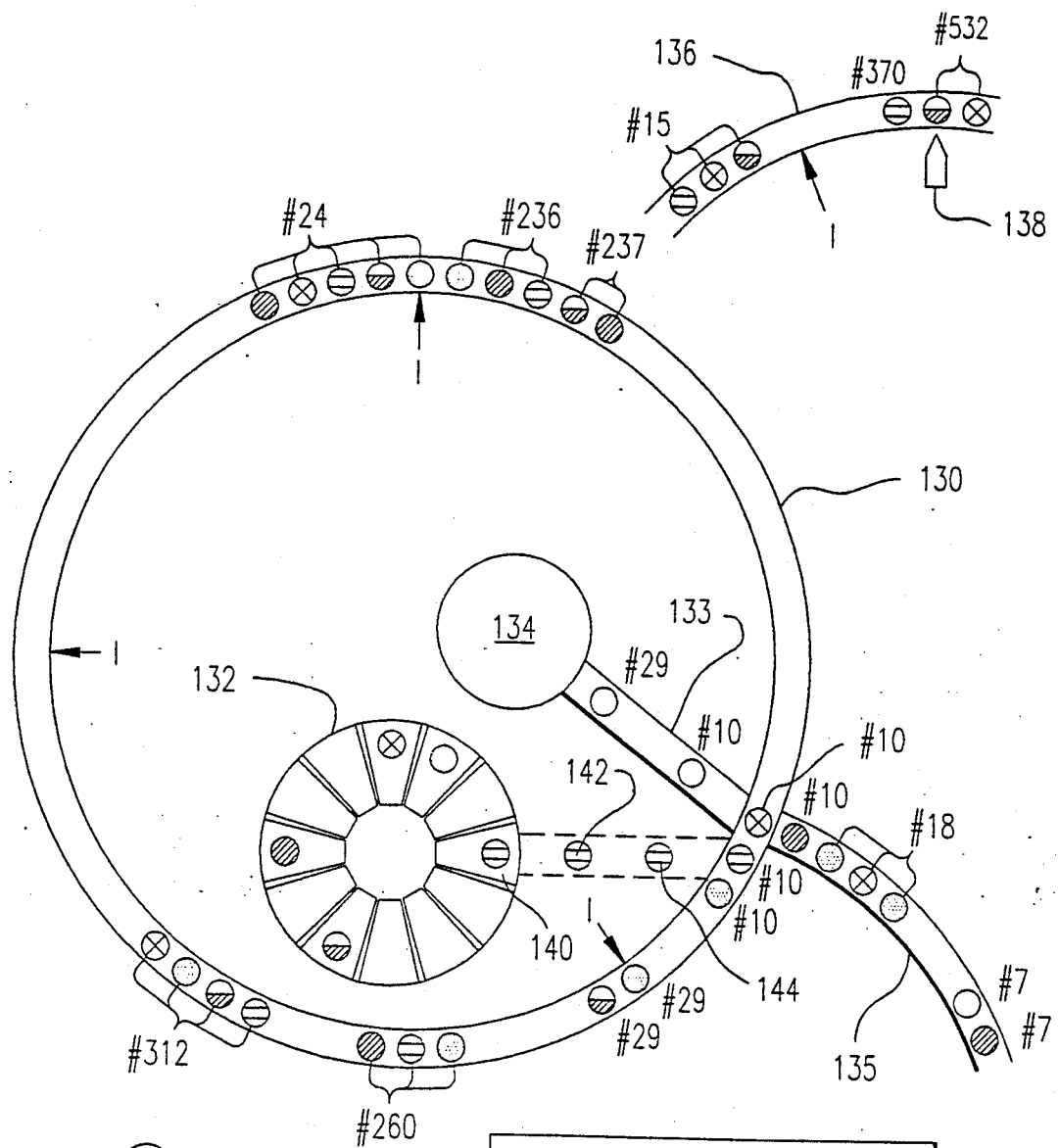
FIG. 7 is an illustration of the display presented to an operator.

Referring now to FIG. 7, there is shown a computer display that operates in conjunction with the instrument 10 of FIG. 2. The display provides a synopsis of all the operations occurring within the instrument 10 at any one time. The display has elements which directly correspond with elements in the instrument 10. For example, a large circular pattern 130 represents the incubation carousel 52, a small circular pattern 132 represents the reagent carousel 40, a pattern 133 and an area 134 represents the path for the sample to the used sample buffer 54, a pattern 135 represents the loading chain 22 from the bar code reader 44, and a curved region 136 represents the path in the detection station to the photomultiplier tube 96 (which is represented in the display by arrow 138). While FIG. 7 shows the location of tubes by circular marks with identifying symbols positioned on the regions 130, 132, 133, 134, 135, and 136, the preferred arrangement has a plurality of circles laid out in the same manner as the "regions" or "patterns" 130, 132, 133, 134, 135, and 136, where each circle represents an incremental step in the circuit travelled by an assay tube in the instrument 10. In addition, filling the circles with different colors, rather than using identifying symbols, provides a better presentation to the scientist or technician observing the immunoassay analyzer display.

The reagents in the carousel are represented by symbols (but would preferably be represented by different colors). A legend appears in the top left hand corner of the display and relates the symbols or colors for the reagents to a particular immunoassay. The legend can expand in size as more reagents 38 are added to the carousel 40. This is accomplished by the bar code reader 71 periodically sensing and outputting sensed reagent 38 information to the computer 12 and the computer 12 updating the legend as appropriate. Hence, if a technician has loaded the analyzer with samples and assay tubes for a particular immunoassay, and the required reagent is not present on the reagent carousel, he or she will be immediately notified of the need for the reagent 38. A separate audible alarm can be provided if a required reagent 38 is missing from the carousel or if the reagent bottle on the carousel 40 is empty (as when the pipetter 60 cannot obtain the required reagent 38 from its bottle). The small circular pattern 132 on the display 16 has an animated rotation as the reagent carousel 40 rotates within the instrument 10 so that the reagent 38 to be pipetted into the assay tube 26 appears in space 140 on the display during a pipetting operation in the instrument 10. Additional animation is provided in the form of successive circular spots 142 and 144 appearing between the space 140 and the large circular ring 130 as the pipetting for a particular immunoassay is being performed.

As the immunoassay tubes 27 are advanced incrementally in the instrument 10, the display 16 is updated simultaneously. Therefore, the assay tubes, which are represented on the display screen by circles with the color or symbol of the particular immunoassay being performed, are shown in the loading path to the pipetting station, advancing through the large circular path of the incubator, proceeding through the curved path to the detector. Several different immunoassay tubes are shown on the incubator path 130 and the detector path 136. Sample tubes, indicated by blank circles, are shown on the path 133 to the waste station 134. A sample number is associated with each sample tube and each assay tube shown on the display. While FIG. 7 shows the sample number adjacent the tube position, the sample number may be presented within the circle for the tube; especially if the immunoassays are represented by color rather than symbols.

The layout of the assay tubes in FIG. 7 illustrates several things. First, the sample order can be varied at the will of the operator. For example, on the incubator path, the assay tubes for sample #29 are preceded by the assay tubes for sample #260 and followed by the assay tubes for sample #10. The sample number (e.g., #29, #260, and #10) would be keyed to a particular patient in a database in the computer 12 so that the immunoassay results would be written to that patient's file after testing. The sample number is dependent on the sample carrier tube 28 being used, and since the carrier tubes are reusable after the sample cup is removed, the technician simply inputs the patient identifier information into the computer 10 for a particular sample carrier tube 28 when that tube will be used. Second, the number and type of immunoassays to be performed on any one sample depends on the number and type of assay tubes selected by the technician. For example, sample #29 only has two tests being performed (e.g., T4 and hCG) while sample #260 has three tests being performed (e.g., T-U, TSH, and hCG). Third, the immunoassays need not be performed one right after another. For example, the assay tubes for the immunoassay tests being performed on sample #312 were followed by several empty spaces in the loading chain 22 of the instrument 10 before the sample and assay tubes for sample #260. Conversely, the tests may be performed one after another as was done in the case of the immunoassays on samples #24, #236 and #237 at the top of the incubator path 130 on the display. Fourth, the sample numbers for the tubes at the photomultiplier tube station 138 tells which tube was just analyzed and which tube will be analyzed next. For example, a table presented on the display at the right hand side shows the DIG concentration for sample #532 was 1.1 ng/ml. The next sample concentration to be presented in the table will be the concentration of T4 for sample #532. The T4 tube for sample 532 may be blinking during the count operation to indicate that the counting and calculating procedure is presently being performed for that immunoassay. The table keeps a running list of the last several concentrations determined by immunoassay and their respective sample identification numbers. Hence, technicians can monitor the table on the display 16 during operation of the immunoassay analyzer to get a quick profile for a particular patient without having to wait until all assays are performed. For example, according to the table, the four immunoassays required for the patient identified by sample #2 have been performed and the detected quantities are presented (e.g, 0.5 ng/ml DIG, 120 mIU/ml hCG, 4.2 mIU/L TSH, and 35% T-U).

Since the immunoassay analyzer has been set up to perform the immunoassays in thirty minutes, a technician can approximate the time required to complete a particular immunoassay on a particular sample by determining its relative position on the display of FIG. 7. Separate time based indicia I can be shown at various points on the display to aid in determining the time remaining before an immunoassay is completed. The display 16 is designed to give the operator a "feel" for what is going on in the instrument and when testing will be completed.

Figure 8A:
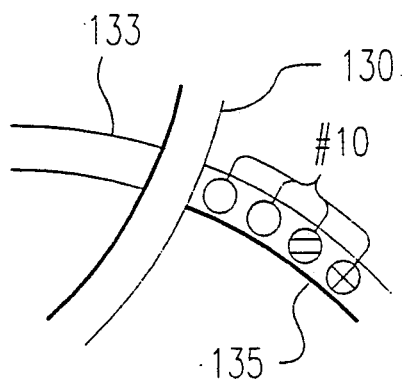
FIGS. 8a to 8d are each partial illustrations of the display of FIG. 7 which show the progressive steps performed by the automated immunoassay analyzer.
Figure 8B:
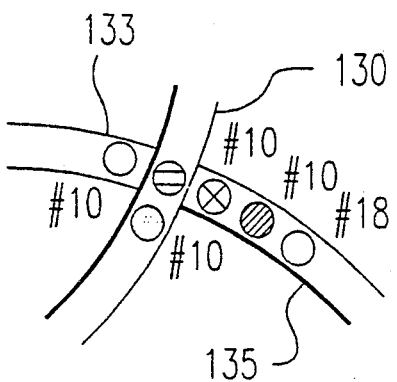
Figure 8C:
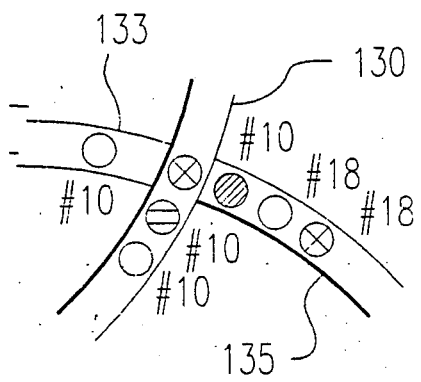
Figure 8D:
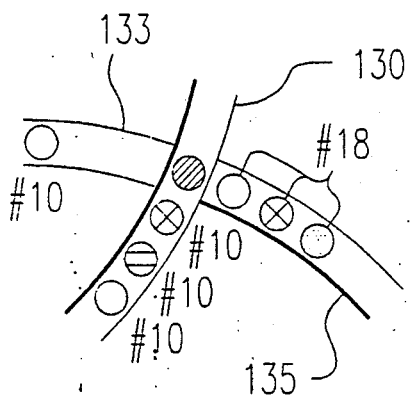

FIGS. 8a–8d illustrate the progress of the sample and assay tubes for sample #10 in the instrument 10 (FIG. 2), as represented on the display (FIG. 7), as the tubes move from the loading chain 22 to the incubation carousel 52. FIG. 8a shows the sample tube 28 and its trailing assay tubes 27 for sample #10 just before pipetting is performed. FIG. 8b shows that the loading chain 22 is advanced twice for the sample tube 28 for sample #10 to pass the incubation carousel 52, and the incubation carousel 52 is incremented once to put the hCG assay tube 27 for sample #10 in position for pipetting. Pipetting is then performed as described above. FIG. 8c shows that the loading chain 22 is advanced once and the incubation carousel 52 is incremented once such that the TSH assay tube 27 is in position for pipetting and the DIG assay tube 27 is on the incubation carousel 52. FIG. 8c also shows the sample tube 28 for sample #10 has moved towards the waste tube collection station 54. FIG. 8d shows the loading chain 22 and incubation carousel 52 have each been incremented once. In FIG. 8d, the sample tube 28 for sample #18 and its trailing assay tubes 27 are now in the same position as sample #10 in FIG. 8a. The next steps will be to increment the incubation carousel 52 once to perform pipetting in the T-U assay tube 27 for sample #10, advance the loading chain 22 twice to move the sample tube for sample #18 past the incubation carousel 52, and then increment the incubation carousel 52 once to put the DIG assay tube 27 for sample #18 in position for pipetting.

Figure 9:
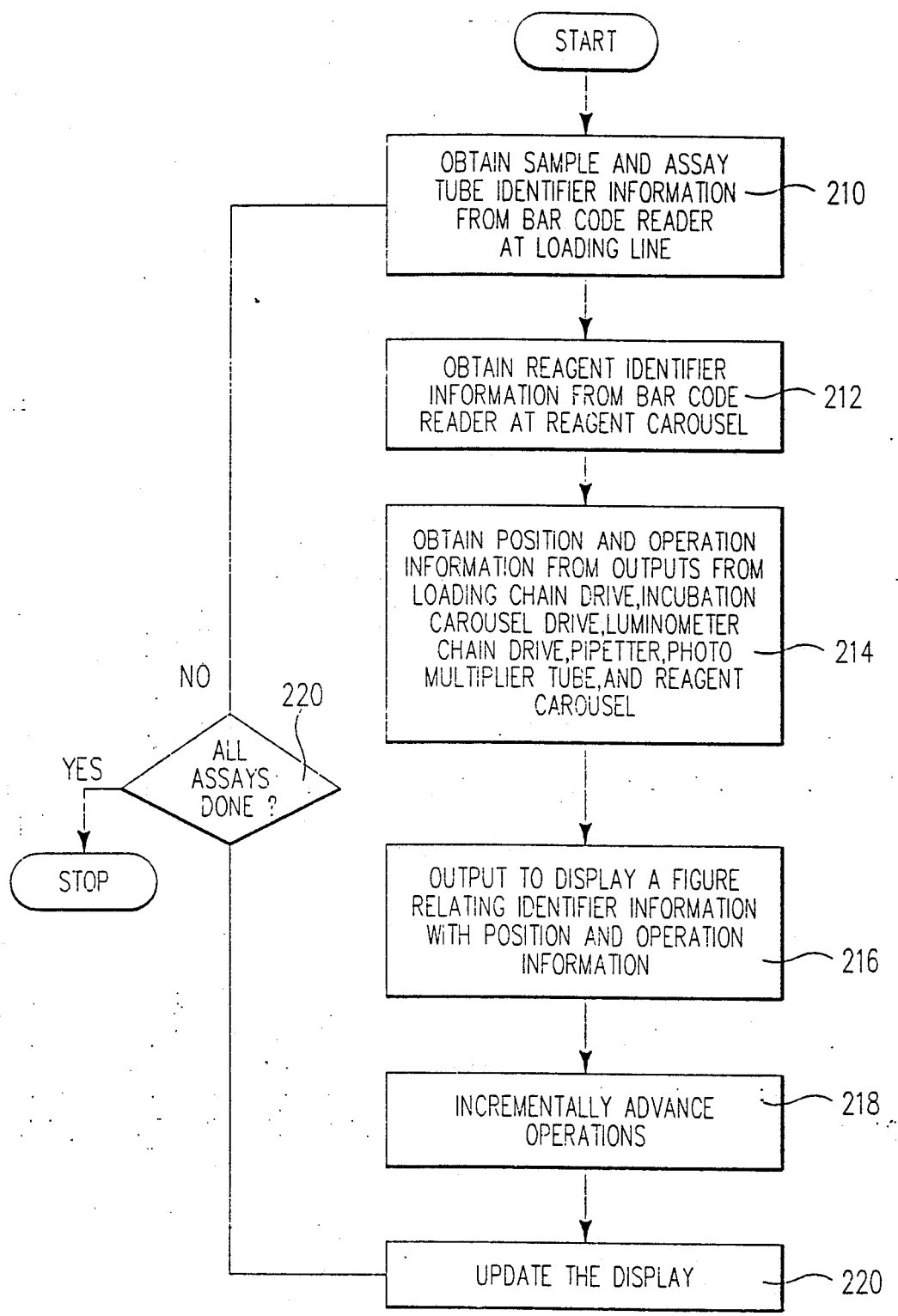
FIG. 9 is a flow chart of the processing steps performed by the computer.

FIG. 9 shows the processing steps performed by the computer 12 for tracking the progress of assay tubes within the instrument 10 and presenting the progress on the display 16 in the manner shown in FIG. 7. At step 210, the sample and assay tube information for the tubes loaded at the loading station is sent from the bar code reader to the computer. At step 212, the reagent identifier information is sent from the bar coder reader at the reagent carousel to the computer. At step 214, the position and operation information from each of the stations in the instrument 10 is sent to the computer. At step 216, the computer outputs to the display 16 a graphic display like that shown in FIG. 7 which relates all the identifier information obtained by the bar code readers with all the position and operational information. At step 218, the circuit paths in the instrument are incrementally advanced. At step 220, the display is updated to reflect the relative positions of the assay tubes within the instrument. With reference back to FIG. 7, it can be seen that once identifier information is input into the system, the progress of the tube in the instrument can be monitored by tracking it in accordance with the positional and operational information. At step 222, it is determined whether all immunoassays in the analyzer have been completed. If so, the operation of the instrument is stopped. If not, the process steps 210-220 are repeated.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. An automated immunoassay analyzer, comprising: an instrument which includes
   (i) a single platform loading station for receiving both sample tubes and assay tubes, said sample tubes containing a sample to be assayed and said assay tubes containing a bound biomaterial for selectively binding an analyte of interest in a sample wherein said different assay tubes may contain a bound biomaterial for binding the same or different analytes of interest,
   (ii) means for identifying said sample tubes and said assay tubes and for generating identifying information for each of said sample tubes and said assay tubes wherein each of said sample tubes is identified and related to one or more of said assay tubes and wherein the number of related assay tubes for each sample tube can be the same or different,
   (iii) a pipetting station having a pipetter for transferring sample from a sample tube to a related assay tube,
   (iv) means for selecting a reagent to be added to said related assay tube for performing a particular assay in said related assay tube and for generating selection information corresponding to the selection of a reagent,
   (v) an incubating station for incubating assay tubes containing sample and reagent,
   (vi) a washing station for washing said bound biomaterial in said assay tube after said assay tubes have been incubated at said incubating station,
   (vii) a detection station for detecting a quantity of analyte bound to said biomaterial in said assay tubes after said assay tubes have been washed at said washing station, said detection station producing a signal proportional to the concentration of analyte for each assay tube, and
   (viii) an assay tube transport pathway connecting said loading station, said pipetting station, said incubating station, said washing station and said detection station, whereby said sample tubes and said assay tubes are separately transported from said loading station to said pipetting station, then said assay tubes are transported to said incubation station then to said washing station and finally to said detection station;
means, connected to said instrument, for monitoring said identifying information obtained from said means for identifying said sample tubes and said assay tubes, said selection information from said means for selecting said reagent, said signal proportional to the concentration of analyte from said detection station and a progression of said assay tubes in said assay tube transport pathway;
control means for automatic controlling of various components of the analyzer in a coordinated manner;
a display connected for said means for monitoring;
means for displaying a pictorial representation of said assay tube transport pathway and said means for selecting a reagent on said display;
means for presenting said identifying information in a pictorial format on said pictorial representation related to said progression of assay tubes in said assay tube transport pathway where the position of said assay tubes in said assay tube transport pathway and the assay being performed in each assay tube can be determined;
means for presenting said selection information on a pictorial format on said pictorial representation where the reagents selected can be determined; and
means for presenting said concentration information for said signal proportional to the quantity of analyte on said display which allows the concentration of an analyte in a particular sample to be determined.

2. An automated immunoassay analyzer as recited in claim 1 wherein said washing station comprises a means to rotate each of said assay tubes at high speed about its longitudinal axis, said assay tubes having a means for catching wash fluid expelled during said high speed rotation.

3. An automated immunoassay analyzer as recited in claim 1 wherein said loading station includes a loading platform with a channel therein for accepting both said sample tubes and said assay tubes at any point along a length of said channel, positioning of said sample tubes and assay tubes within said channel in said loading platform determining a processing order of said sample tubes and said assay tubes.

4. An automated immunoassay analyzer as recited in claim 1 wherein said means for selecting a reagent includes a reagent carousel with an associated bar code reader.

5. An automated immunoassay analyzer as recited in claim 4 wherein said reagent carousel has slots for holding a plurality of reagents, each of which has bar coded identifying information, and said means for selecting a reagent further includes a means for periodically determining a position for each reagent on said reagent carousel.

6. An automated immunoassay analyzer as recited in claim 1 wherein said means for identifying said sample and said assay tubes includes a bar code reader.

7. An automated immunoassay analyzer as recited in claim 1 wherein said detection station includes a means for detecting light.

8. An automated immunoassay analyzer as recited in claim 7 wherein said means for detecting light is a photomultiplier tube.

9. An automated immunoassay analyzer as recited in claim 1 further comprising a means for determining when a reagent is required by said means for selecting such that said reagent may be added.

10. An automated immunoassay analyzer as recited in claim 1 wherein said pipettor used at said pipetting station to transfer said sample from said sample tube to said related assay tube is also used in conjunction with said means for selecting a reagent to transfer a reagent to said related assay tube.

11. In an automated chemical analysis instrument having multiple stations for performing different functions on samples contained in test vessels, a pathway connecting each of the stations along which the test vessels are transported from one station to the next, and a device located at an end of the pathway for detecting a parameter for each of the samples contained in the test vessels, the improvement comprising:
- a display;
- means for assessing the state of operation of each of said multiple stations;
- means for tracking the progress of each of said test vessels on said pathway connecting each of the different stations;
- means for detecting a parameter of each of the test vessels; and
- means for presenting a pictorial image on said display of said pathway connecting said multiple stations, said pathway connecting each of the different stations, and said test vessels, said means for presenting providing both a numerical presentation of said detected parameter and a pictorial presentation of the position of each of said test vessels on said pathway connecting each of the different stations, said means for presenting being supplied with status information from said means for assessing and said means for tracking and numerical information from said means for detecting.

* * * * *